United States Patent
Choi et al.

(10) Patent No.: US 6,582,879 B2
(45) Date of Patent: Jun. 24, 2003

(54) REACTIVE PHOTO ACID-GENERATING AGENT AND HEAT-RESISTANT PHOTORESIST COMPOSITION WITH POLYAMIDE PRECURSOR

(75) Inventors: Kil-Yeong Choi, Daejeon (KR); Moon Young Jin, Daejeon (KR); Jong Chan Won, Daejeon (KR); Sang Yeol Choi, Jeonra-namdo (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 108 days.

(21) Appl. No.: 09/817,273

(22) Filed: Mar. 27, 2001

(65) Prior Publication Data

US 2003/0064315 A1 Apr. 3, 2003

(51) Int. Cl.$^7$ .................. G03F 7/004; C07C 315/00
(52) U.S. Cl. .................. 430/270.1; 430/920; 430/921; 568/28; 568/30; 568/34
(58) Field of Search ................. 430/270.1, 921, 430/920; 568/28, 30, 34

(56) References Cited

U.S. PATENT DOCUMENTS 4,927,736 A  5/1990  Mueller et al.

FOREIGN PATENT DOCUMENTS

| DE | 24 37 348 | | 8/1974 |
| EP | 502 400 A1 | | 9/1992 |
| WO | 94/10608 | * | 5/1994 |

OTHER PUBLICATIONS

*Polym. Eng. Sci.*, Kerwin & Goldrick, vol. 11, p. 426–430 (1971).
*Polymers for Advanced Technology*, vol. 4, pp. 277–287, May 1993.

\* cited by examiner

Primary Examiner—Rosemary Ashton
(74) *Attorney, Agent, or Firm*—Finnegan, Henderson, Farabow, Garrett & Dunner, L.L.P.

(57) ABSTRACT

The present invention relates to a reactive photo acid-generating agent and a heat-resistant photoresist composition comprising the same. In particularly, the present invention relates to the heat-resistant photoresist composition comprising the photo acid-generating agent expressed by the following formula (1), which can increase the degree of polymerization, and polyamide oligomers having acetal or its cyclized derivatives, which have an ability of that light-exposed area is dissolved in the developer and light-unexposed area is convertible to a heat-resistant polymer in the latter heating process and thus, it can be used for passivation layer, buffer coat or layer-insulating film of the multilayer printed circuit board,

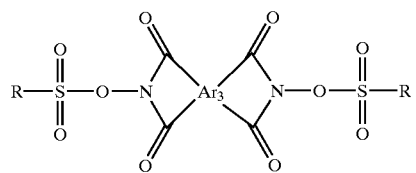

(1)

wherein

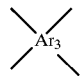

and R are the same as defined in the detailed description of the Invention.

4 Claims, No Drawings

REACTIVE PHOTO ACID-GENERATING AGENT AND HEAT-RESISTANT PHOTORESIST COMPOSITION WITH POLYAMIDE PRECURSOR

BACKGROUND OF THE INVENTION

Field of the Invention

The present invention relates to a reactive photo acid-generating agent and a heat-resistant photoresist composition comprising the same. In particularly, the present invention relates to the heat-resistant photoresist composition comprising the photo acid-generating agent expressed by the following formula (1), which can increase the degree of polymerization, and polyamide oligomers having acetal or its cyclized derivatives, which have an ability of that light-exposed area is dissolved in the developer and light-unexposed area is convertible to a heat-resistant polymer in the latter heating process and thus, it can be used for passivation layer, buffer coat or layer-insulating film of the multilayer printed circuit board,

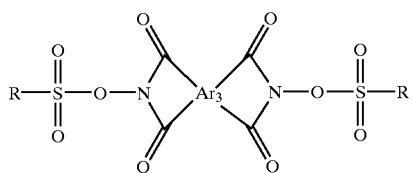

(1)

wherein

represent

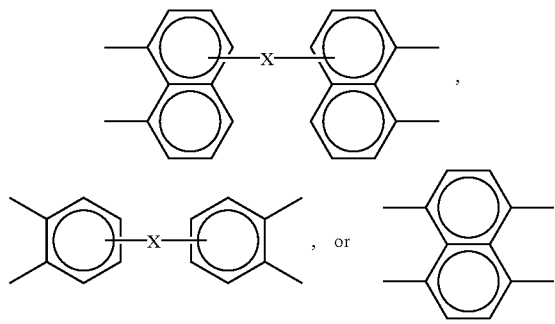

in which X represents —CH$_2$—, —O—, —S—, —SO$_2$—, —CO—, —NHCO—, —C(CH$_3$)$_2$—, —C(CF$_3$)$_2$—, or

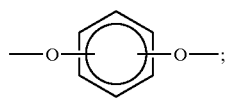

and R represents —CH$_3$, —C$_2$H$_5$, —C$_3$H$_7$, —C$_4$H$_9$, —CF$_3$,

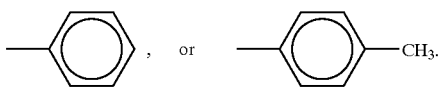

Polyimide is useful for layer-insulating films of surface protection layers, semiconductor dielectric, multi-layer chip module, and the like due to high stability against heat and chemicals.

Conventionally, complicated lithography processes such as photoresist coating, prebaking, UV exposure, developing of photoresist, etching of passivation layer and removing of photoresist are required for patterned heat-resistant insulating layer to make electrical connection with the conductor wiring between upper and lower layer or multi-layers.

Therefore, there have been intensive researches on the preparation of direct polyimide pattern as a photosensitive compound with polyimides or polyamide precursors. If the heat-resistant materials have a function of photoresist, several steps for lithographic process such as a photoresist coating and its removing become unnecessary in making via holes for wiring. Moreover, it can reduce the use of resist and chemicals. Accordingly, the use of heat-resistant photoresist can greatly simplify and make the whole process efficient. On top of that it can prevent the degraded resolution and reproducibility which can be happened during the process of etching and resist removal. Since while photoresist is generally removed out from the top of passivation layer after lithographic processes such as light-exposure, development and etching for photoresist, the heat-resistant photoresist of the present invention remains in the semiconductor permanently, it provides not only insulation, heat resistance, mechanical and low dielectric properties which are required as semiconductor materials, but also excellent photosensitivity, resolution, transparency and developing properties which are required as photosensitive materials.

Typical examples of photosensitive chemicals are polyamic acid derivatives containing side chains bonded through ether linkage, ester linkage, amide linkage or acid ammonium salt.

The first attempt for photosensitive polyimides was using polyamic acid chromate as sensitizer [Kerwin and Goldrick, Polym: Eng. Sci., 11, 426 (1971)], which was failed to be commercialized since it used an inorganic metal and the storage period was too short.

Negative photosensitive polyamides using photo-crosslinkable polyimide precursors having esters or ionic groups as pendant groups are disclosed in German Patent No. 2,437,348, and this system indicated the possibility of applying polyimides in applications of semiconductors since soluble photosensitive polyamic acid and very little amount of a metallic ion were used. However, in general the negative heat-resistant photoresists may give us lower resolution of relief pattern due to particles or cracks present on the photomask. Further, the resolution may be deteriorated by swelling of the relief pattern, since organic solvents are used for the developer.

On the other hand, U.S. Pat. No. 4,927,736 discloses positive heat-resistant photoresists prepared from aromatic hydroxy polyimides with covalently attached or solution blended naphtoquinone diazide (NQ) as a photosensitive agent. Since aromatic hydroxy polyimides themselves absorbs large amount of light, and consequently lowering the quantum efficiency, a large amount of a photosensitive agent should be used to improve the quantum efficiency. Besides, a large amount of polar residues of used photosensitive agent remains in the film and polar groups such as —OHs also remain in the main chain of the polymer, and thus the dielectric constant is increased and heat-resistance is decreased.

Other methods have been reported by introducing a chemical-amplifying acid-sensitive group to aromatic hydroxy polyimides [*Polymers for Advanced Technology*, vol. 4, 277, 287, 1992] or polyamic t-butyl ester polyimide precursors, [European Patent Publication No. 0502400A1] to improve photosensitivity and resolution. In these methods, —OH or —COOH groups are blocked by a chemical-amplifying acid-sensitive group, thereby the solubility in aqueous alkali solutions is decreased. Then the acid produced by the photo-reaction of photo acid-generating agent decomposes the acid-sensitive group to recover —OH or —COOH groups which help the polymers to be soluble in developer solutions. Even though the quantum efficiency can be improved by the treatments, in the case of using aromatic polyimides containing hydroxyl group, the —OH groups generated after the thermal treatment for curing may remain in the film which increase the dielectric constant of the film; and in the case of using polyamic t-butyl ester polyimide precursors, the dielectric constant is increased and the heat-resistance is decreased because too much of photo acid-generating agent should be used.

SUMMARY OF THE INVENTION

The inventors have made intensive efforts to fundamentally solve the problems of the conventional heat-resistant photoresists such as, increase of electric constant due to hydroxyl groups generated after the thermal treatment for curing, decrease of heat-resistance due to the remaining acid-generating material in the film after the development, and especially poor flatness due to the high viscosity of polymers in the preparation of multiplayer circuit board, and to improve the photosensitivity. As a result, inventors have discovered novel positive heat-resistant photoresists enables of achieving high quantum efficiency through chemical-amplifying photosensitive agent, low dielectric constant and high heat-resistance by minimizing the use of photosensitive agent and by eliminating the unreacted polar groups, and better flatness in the preparation of multiplayer circuit board.

Accordingly, an object of the present invention is to provide an aromatic bissulphonic diamide compound containing a photo acid-generating agent.

Another object of this invention is to provide a novel heat-resistant photoresist composition comprising polyamide oligomers having ester groups as pendant groups and a photo acid-generating agent in an appropriate ratio to obtain advantages in minimizing post-exposure baking process and post-exposure delay effect owing to have.

DETAILED DESCRIPTION OF THE INVENTION

The present invention is characterized by a photo acid-generating agent expressed by the following formula (1),

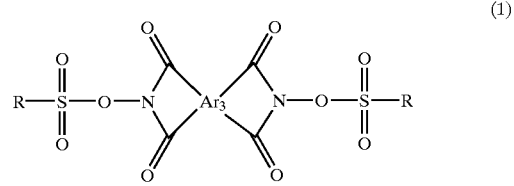

wherein

and R are the same as defined above.

The present invention is also characterized by a positive heat-resistant photoresist composition comprising the photo acid-generating agent expressed by the following formula (1) and the polyamide oligomer having ester groups as pendant groups expressed by the following formula (2),

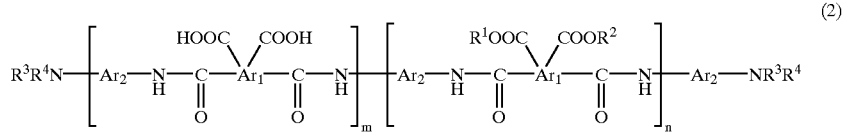

wherein $Ar_1$ is a quaternary aromatic group which is selected from the group consisting of

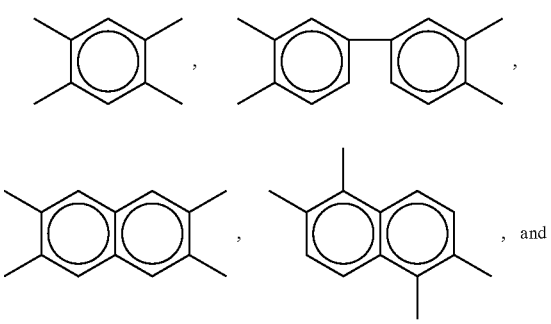

$Ar_2$ is a secondary aromatic group which is selected from the group consisting of

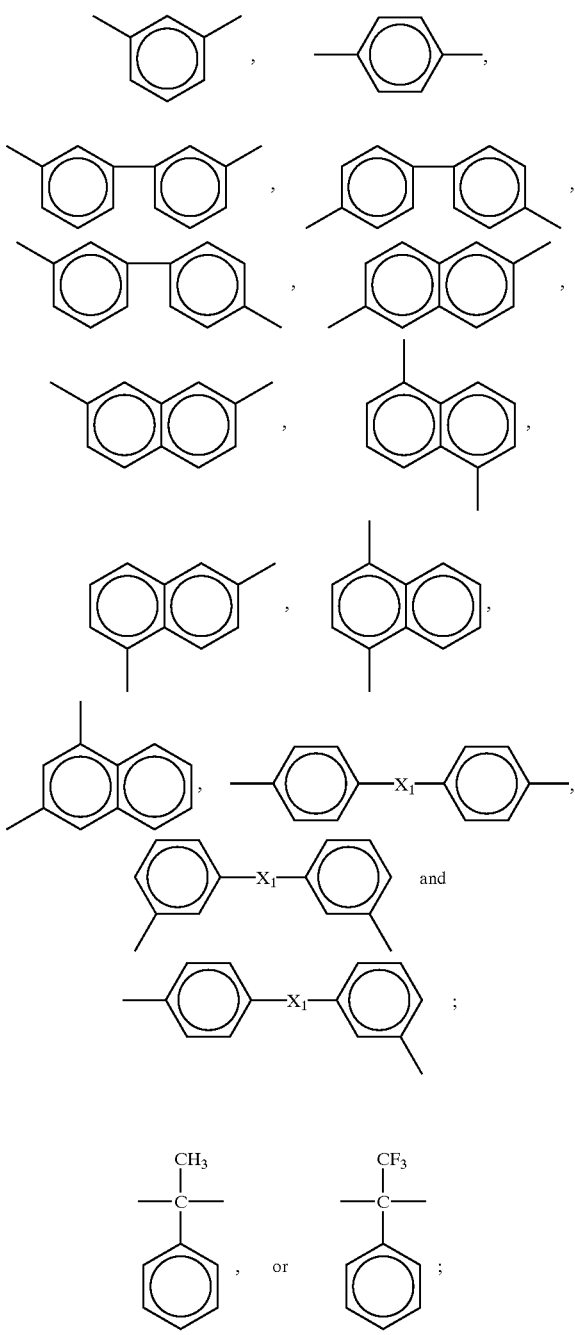

R¹ and R² are independently a hydrogen atom or $C_1$–$C_{10}$ alkyl having

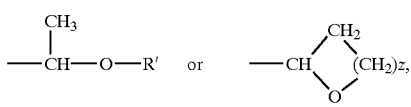

wherein R¹ is a $C_1$–$C_6$ alkyl such as ethyl, propyl, isopropyl, butyl, isobutyl, t-butyl and cyclohexyl; and z is an integer of 1–4 (however, excluding the case when both R¹ and R² are hydrogen atoms);

R³ and R⁴ are independently a hydrogen atom, $$-\overset{O}{\underset{}{C}}-OC_2H_5, \text{ or}$$ (benzene ring with two acetyl groups)

which exist at the terminal portion of the molecule added to adjust the molecular weight of the oligomer;

a degree of polymerization (m+n) is 3–50; and a polyamide oligomer is a homopolymer or a copolymer prepared by the combination of $Ar^1$ and $Ar^2$.

Hereunder is given the detailed description of the present invention.

A aromatic bissulphonic diamide compound according to the present invention expressed by the above formula (1) is a photo acid-generating agent that generates acids by absorbing light with longer than 300 nm of wavelength. It can improve the quantum efficiency and its amount can be reduced because it generates two equivalents of acids for a unit molecule. Also, it helps to increase the mechanical property, since the diimide compounds formed easily through pyrolysis increases the molecular weight through imides exchange reaction with oligomers.

Accordingly, the present invention includes a heat-resistant photoresist composition expressed by the above formula (2), which contains polyamide oligomer containing ester groups as pedant groups, together with the photo acid-generating agent expressed by formula (1). The content of the reactive photo acid-generating agent expressed by formula (1) is in the range of 0.3–15wt.% to the polyamide oligomer. If too much photo acid-generating agent is used, dielectric property, mechanical property and heat resistance worsen since the molecular weight of the polymer is not sufficient, and complete holes are not formed due to the poor optical transperancy; and otherwise if too less is used, the resolution becomes poor and mechanical strength worsens, since the acid is insufficient to function as an acid generating agent. Also, the polyamide oligomer contained in the heat-resistant photoresist composition of the present invention can improve planerization in the coating process due its low molecular weight, and it can improve the heat resistance and mechanical strength since the pyrolyzed diimide reacts with polyamide acid and functions as a sensitizer.

Ester groups contained as pedant groups in polyamide oligomers expressed by formula (2) can be carboxyl groups or acid-sensitive esters having ethers or its cyclized derivatives. Also, a low-dielectric polyimide film with excellent heat resistance and mechanical property can be prepared through the reaction of the polyamide oligomer and the photo acid-generating agent. In additions, holes formed in the pretreatment is filled due to the reduced viscosity by the low molecular weight and the planarized coating is performed by the final heat treatment.

The following Scheme 1 is an example of the reaction of the photo acid-generating agent expressed by formula (1) and the polyamide oligomers containing esters as pedant groups expressed by formula (2), Scheme 1

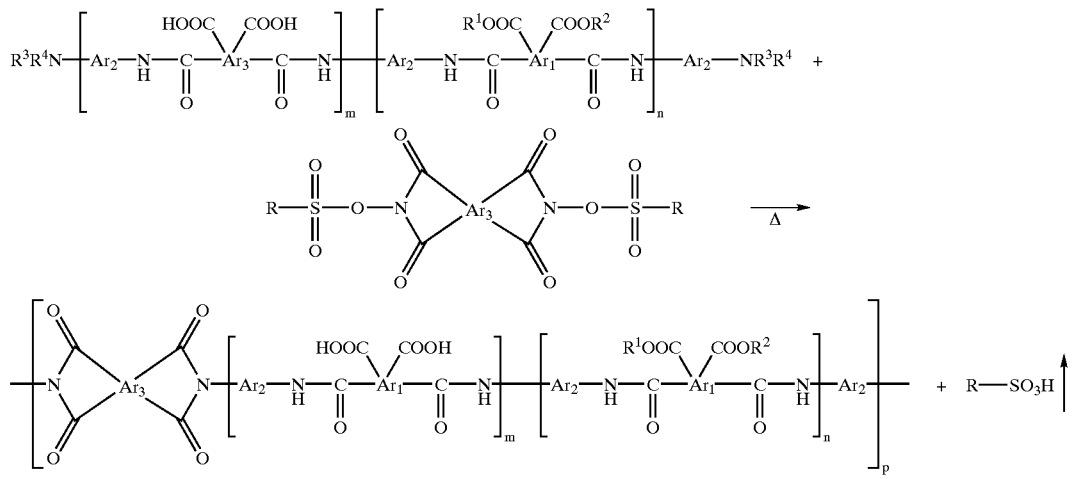

wherein $Ar_1$, $Ar_2$, $Ar_3$, R, $R^1$, $R^2$, $R^3$, $R^4$, m and n are the same as defined above.

As mentioned earlier, the heat-resistant photoresist composition according to the present invention, obtained by mixing a polyamide oligomer and a reactive photo acid-generating agent, is treated by the following process of coating, light-exposing, pre-exposure heating, developing and post-exposure baking process to provide positive photosensitive material having low-dielectric property. The light-exposed area, where the heat-resistant photoresist composition of the present invention is coated, generates acids through a decomposition of the photo acid-generating agent. Acids transform esters of the polyamide oligomer to the corresponding carboxylic acid, which transform further to polyamic acid through the acid-amplification (chain reaction of the acid) and thus the light-exposed area can be removed by dissolving in a developer. On the other hand, the light-unexposed area remains insoluble as polyamide oligomer containg pendant ester group is not dissolved during the development process. Bissulpihonic diiimide compound containing a photo acid-generating group decomposes in the post-heating process. So, the photo acid-generating group is volatilized and aromatic groups are transformed into diimide monomers. Also, the ester group of the polyamide oligomer containing ester group as pendant groups is removed by overcoming the activation energy barrier. The resultant diimide compound and polyamic acid oligomer forms the corresponding polyimide polymer having much higher molecular weight through trans-imidization process. Thus, the cracking of film, which may occur with oligomers having low molecular weight, can be prevented since the mechanical strength is increased.

Namely, when a heat-resistant photoresist composition obtained by mixing a polyamide and a photo acid-generating agent is applied on the substrates and visible or UV light are exposed through a patterned photo mask, the acid-sensitive esters are transformed to carboxyl groups. Consequently, the exposed area becomes soluble to an aqueous alkaline solution such as tetramethylammonium hydroxide(TMAH). On the other hand, as the unexposed area to light has low solubility in an alkaline solution, positive pattern of polyamide can be formed. Heating of this patterned light-unexposed area converts the acid-sensitive ester groups to carboxyl groups, and further heating causes carboxyl groups to react with neighboring amide groups to form imide groups which provides high heat resistance and low dielectric property.

This polyimides have a great heat resistance as to be resistant to temperature over 520° C. Besides, the acid-sensitive acetal and/or its cyclic derivative decomposes to form volatile chemicals having low-molecular weight (for example, ethyl vinyl ether, dihydropyran, alkyl, alkene, ether, or cyclized alkene ether derivative thereof) and nothing remains in the film. Thus, the dielectric constant becomes much lower than that of conventional photosensitive polyimides(PSPI) using naphthoquinone diazide(NQ) as a photosensitizer.

Namely, ester groups are used in the present invention to heat-resistant reaction in place of hydroxyl groups, which deteriorate low-dielectric property, heat resistance and electrical property. And, a large amount of acids is generated while photo acid-generating agent and acid-sensitive groups used for chemical amplification process are decomposed by light or acid, and can activate decomposition of acid-sensitive groups. Consequently, the quantum efficiency is improved and the degree of polymerization is increased since reactive photo acid-generating agent participates in the polyimide polymerization process. Thus deterioration of various properties including dielectric property can be minimized.

Concentration of the acid-sensitive group ($-COOR^1$) contained in the polyamide oligomer expressed by formula (2) which is contained in the heat-resistant photoresist according to the present invention is the range of 1%–90%, and preferably in the range of 15%–60%. If the concentration of acid-sensitive group ($-COOR^1$) is too high, the developing rate slows down, and therefore, long light-exposure time to light or a large amount of photo acid-generating agent becomes necessary. Otherwise, if the concentration of the acid-sensitive group ($-COOR^1$) is too low, there may be problems of poor resolution, decreased thickness, and difficulty in controlling developing rate due to extremely rapid development.

The heat-resistant photoresist according to the present invention can be prepared in a solution state. Examples include dimethylsulfoxide, hexamethylphosphoamide, dimethylacetamide, dimethylformamide, N-methyl-2-pyrolidone, γ-butyrolactone, diglyme, butoxyethanol and propyleneglycolmethylether acetate (PGMEA), and a small amount of the solvent with poor solubility, such as toluene, xylene, methanol, isopropyl alcohol, may be also used. An amount of the solvent varies with a solubility of a polyamide precursor, but its kind is not limited. However, ester-family or ether-family solvent prefers to amide-family solvent.

Also, combination of two or more of the solvents can be used to improve the uniformity, thickness adjustment and adhesion of the film. The heat-resistant photoresist composition is prepared in the concentration of 10–70wt %, and it can be adjusted according to the desired coating thickness.

For a film formation using the heat-resistant photoresist composition, any one of spin coating, bar coating or doctor blade method, which are commonly used in the electronics industry, may be used. Proper drying temperature for film formation is 40–150° C.

If the drying temperature is too low, longer drying time is required; and if it is too high, the transparency reduces since the decomposition of acid-sensitive group by the pyrolysis and the formation of imide groups, which darkens color.

The proper exposure light is visible or UV with 200–500 nm wavelength, and it is more proper to use a light exposing device equipped with a monochrome filter in order to get better resolution and processibility. In the present invention, any particular equipment or light-exposure device is not specified.

Light exposure time can be varied with experiment conditions. In the present invention, when a UV exposure device equipped with a 365 nm-filter was used, the light exposure time could be varied from 10 sec to 200 sec. If a stronger light exposure device is used, the light exposure time can be shortened. The energy of the exposure light is determined with an energy meter. The resolution is determined in depth and width with a profilometer, and the cross section of the film is identified with a scanning electronic microscope.

Polyamide oligomer used in the present invention is a well-known compound easily prepared by known methods. It can be prepared from an aromatic diamine and an aromatic dicarboxylic acid or its derivative as in the following Scheme 2,

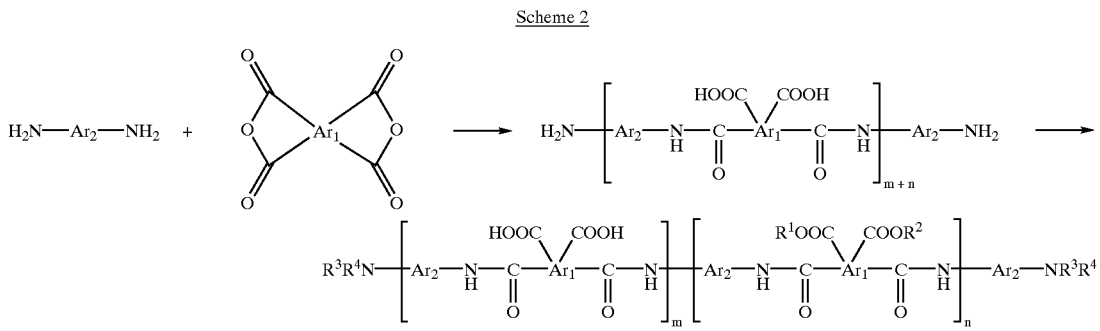

Scheme 2 wherein $Ar_1$, $Ar_2$, $R^1$, $R^2$, $R^3$, $R^4$, m and n are the same as defined above.

In the above Scheme 2, the polymerization temperature is recommended to be under 50° C., and preferably under 20° C. If the polymerization temperature is too high, solvent-insoluble polyimide may form due to the excessive reaction. Also, various acid-sensitive groups (—$COOR^1$) expressed in Scheme 2 may be included in the monopolymer or copolymer in order to control the development rate and the photosensitivity. For a method of bonding the acid-sensitive ester group to the polymer, it is recommendable to use excess amount of alkyl vinyl ether or cyclized alkene ether derivative in the presence of an acidic catalyst. Acid catalyst used is a strong acid such as p-toluenesulfonic acid, phosphoric acid and hydrochloric acid. The introduction of acid-sensitive agents is preferred to perform at room temperature or below. If the reaction temperature is high, the pyrolysis of acid-sensitive group and formation of polyimide may occur.

Hereunder is given more detailed description of the present invention by examples and preparing examples. However, they should be construed as limiting the scope of the present invention.

PREPARING EXAMPLE 1

After placing 12 g of 4,4'-oxydianiline (hereunder referred to as "ODA") in a 250-mL 3-necked flask, the same was dissolved with N-methyl-2-pyrrolidinone (hereunder referred to as "NMP"). Maintaining the temperature at 0° C., 26.62 g of 4,4'-(hexafluoroisopropylidene)diphthalic acid anhydride (hereunder referred to as "6FDA") was added and the same was reacted while stirring for 2 hr under $N_2$. After adding and dissolving 0.76 g of p-toluenesulfonic acid in the viscous polymer solution, 10.08 g (1 equivalent) of 3,4-dihydro-(2H)-pyran was added and esterified for 4 hr while stirring. After precipitating the reactant in a water/methanol mixture using a Waring Blender, and washing the same 3 times, it was dried for 3 days at room temperature in vacuum to obtain a white polymer. Table 1 shows the viscosity of polymers obtained by varying the ODA amount used in the polymerization.

TABLE 1

| Samples | PAOF-1-1 | PAOF-2-1 | PAOF-3-1 | PAOF-4-1 | PAOF-5-1 |
| --- | --- | --- | --- | --- | --- |
| ODA amount | 12 g | 12.06 g | 12.12 g | 12.24 g | 12.36 g |
| Viscosity (dL/g) | 0.38 | 0.34 | 0.31 | 0.28 | 0.24 |

PREPARING EXAMPLE 2

Polyamide oligomer was prepared as in the Preparing Example 1. However, 1.2 g of ODA and 26.62 g of 6FDA were added and reacted for 2 hr, and the addition amount of 3,4-dihydro-(2H)-pyran was changed to 2, 4, 12 and 20 equivalents respectively to adjust the concentration of acid-sensitive tetrahydropyranyl ester group. The concentration of tetrahydropyranyl ester group was determined using $^1$H-NMR, and the result is shown in Table 2.

TABLE 2

| Sample | PAOFA-1-1 | PAOF-1-2 | PAOF-1-4 | PAOF-1-12 | PAOF-1-20 |
| --- | --- | --- | --- | --- | --- |
| Equivalents of 3,4-Dihydro-(2H)-pyran | 1 equiv. | 2 equiv. | 4 equiv. | 12 equiv. | 20 equiv. |
| Concentration of Tetrahydropyranyl Ester Group (%) | 25 | 34 | 47 | 78 | 85 |

PREPARING EXAMPLE 3

After placing 11.9 g of 4,4'-methyldianiline (hereunder referred to as "MDA") in a 250-mL 3-necked flask, the same was dissolved with NMP. Maintaining a temperature at 0° C., 26.62 g of 6FDA was added and the same was reacted while stirring for 2 hr under $N_2$. After adding 0.2 g of ethyl carbamate, the same was stirred for 10 min. After adding and dissolving 0.76 g of p-toluenesulfonic acid in the viscous polymer solution, 40.32 g of 3,4-dihydro-(2H)-pyran was added and esterified for 4 hr while stirring. After precipitating the reactant in a water/methanol mixture using a Waring Blender, and washing the same 3 times, it was dried for 3 days at room temperature in vacuum to obtain a white polymer (PAMF-1-4). Its viscosity was 0.35 dL/g.

PREPARING EXAMPLE 4

After placing 6.80 g of 1,3-phenylenediamine (hereunder referred to as "m-PD") in a 250-mL 3-necked flask, the same was dissolved with NMP. Maintaining the temperature at 0° C., 26.62 g of 6FDA was added and the same was reacted while stirring for 2 hr under $N_2$. After adding and dissolving 0.76 g of p-toluenesulfonic acid in the viscous polymer solution, 40.32 g of 3,4-dihydro-(2H)-pyran was added and esterified for 4 hr while stirring. A small amount of phthalic acid anhydride was added and the same was stirred for 10 min. After precipitating the reactant in a water/methanol mixture using a Waring Blender, and washing the same 3 times, it was dried for 3 days at room temperature in vacuum to obtain a white polymer (PAmPF-2-4). Its viscosity was 0.31 dL/g.

PREPARING EXAMPLE 5

After placing 12 g of ODA in a 250-mL 3-necked flask, the same was dissolved with NMP. Maintaining the temperature at 0° C., 21.1 g of 4,4'-(isopropylidene)diphthalic acid anhydride (hereunder referred to as 6HDA) was added and the same was reacted while stirring for 2 hr under $N_2$. After adding and dissolving 0.76 g of p-toluenesulfonic acid in the viscous polymer solution, 40.32 g of 3,4-dihydro-(2H)-pyran was added and esterified for 4 hr while stirring. And then, 0.48 g of ODA was added and the same was stirred for 10 min. After precipitating the reactant in a water/methanol mixture using a Waring Blender, and washing the same 3 times, it was dried for 3 days at room temperature in vacuum to obtain a white polymer (PAOM-1-4). Its viscosity was 0.36 dL/g.

PREPARING EXAMPLE 6

After placing 1.2 g of ODA in a 250-mL 3-necked flask, the same was dissolved with NMP. Maintaining the temperature at 0° C., 26.6 g of 6FDA was added and the same was reacted while stirring for 2 hr under $N_2$. After adding 0.48 g, of ODA, the same was added for 10 min. After adding and dissolving 0.76 g of p-toluenesulfonic acid in the viscous polymer solution, 34.56 g of ethyl vinyl ether was added and esterified for 4 hr while stirring. And then, a small amount of phthalic acid anhydride was added and the same was stirred for 10 min. After precipitating the reactant in a water/methanol mixture using a Waring Blender, and washing the same 3 times, it was dried for 3 days at room temperature in vacuum to obtain a white polymer (PAOFE-1-4). Its viscosity was 0.32 dL/g.

PREPARING EXAMPLE 7

Polyamic acid oligomer was prepared as in the Preparing Example 6. However, alkyl vinyl ether or cyclized alkene ether was added instead of ethyl vinyl ether as in the following Table 3. The viscosity of the obtained polyamic acid oligomer with ester side chain is shown in Table 3.

TABLE 3

| Polymer | Alkyl Vinyl Ether | Amount of Acid-sensitive Group | Inherent Viscosity (dL/g) |
| --- | --- | --- | --- |
| PAOFP-1-8 | Propyl vinyl ether | 8 mol equiv. | 0.32 |
| PAOFi-1-8 | Isopropyl vinyl ether | 8 mol equiv. | 0.35 |
| PAOFnB-1-8 | n-Butyl vinyl ether | 8 mol equiv. | 0.33 |
| PAOFtB-1-8 | tert-Butyl vinyl ether | 8 mol equiv. | 0.29 |
| PAOFH-1-8 | Cyclohexyl vinyl ether | 8 mol equiv. | 0.31 |
| PAOFF-1-4 | 2,3-Dihydrofuran | 4 mol equiv. | 0.32 |

EXAMPLE 1

Preparation of N,N'-Ditrifluoromethansulphonyloxy-4,4'-(phenylene-1,3-dioxy)dinaphthalene-1,8:1',8'-tetracarboxylic Imide (TfSPODNI)

(1) Preparation of 4,4'-(Phenylene-1,3-dioxy)dinaphthalene-1,8:1',8'-tetracarboxylic Anhydride (PODNA)

After adding 3.97 g of resorcinol and 9.92 g of potassium carbonate anhydride in 150 mL of dimethylformamide (hereunder referred to as "DMF") in a 250 mL flask equipped with a condenser and a thermometer at 70° C. under $N_2$, 20.00 g of 4-bromo-1,8-naphtalic acid anhydride was added while stilling After 30 min of stirring, the same was heated to 140° C. and this temperature was maintained for 12 hr for reaction. After cooling the reaction solution, the same was precipitated in 500 mL of iced distilled water and filtered. After washing the product with distilled water, the same was dried at 100° C. and recrystallized with DMF and extracted with 1/2 mixture of acetic acid anhydride and acetic acid to obtain pale-yellow 4,4-(phenylene-1,3-dioxy)dinaphthalene-1,8:1',8'-tetracarboxylic anhydride (PODNA) with 71% of yield.

$^1$H-NMR (DMSO-$d_6$) δ 8.77 (d, 2H), 8.60 (d, 2H), 8.49 (d, 2H), 7.95 (t, 2H), 7.72 (t, 1H), 7.38 (s, 4H), 7.32 (d, 2H), 7.21 (d, 2H); FT-IR :1765, 1728 cm$^{-1}$ (C=O); m/e: 502 (theoretical value: 502.44).

(2) Preparation of N,N'-Dihydroxy-4,4'-(phenylene-1,3-dioxy)dinaphthalene-1,8:1',8'-tetracarboxylic Imide (HPODNI)

After adding 2.51 g of PODNA and 0.83 g of hydroxylamine hydrochloride in 40 mL of pyridine in a 100 mL flask equipped with a condenser and a thermometer, the same was heated to 90° C. and stirred for 2 hr. After the reaction, pyridine was distilled under reduced pressure, and the product was precipitated in distilled water, and then filtered. After drying the same at 100° C., 2.47 g (93%) of N,N'-dihyroxy-4,4'-(phenylene-1,3-dioxy)dinaphthalene-1,8:1',8'-tetracarboxylic Imide (HPODNI) was obtained.

$^1$H-NMR δ 10.70 (s, 2H, —OH), 8.69 (d, 2H), 8.58 (d, 2H), 8.47 (d, 2H), 7.92 (t, 2H), 7.68 (t, 1H), 7.34 (s, 1H), 7.29 (d, 2H), 7.20 (d, 2H).

(3) Preparation N,N'-Ditrifluoromethanesulfonyloxy-4,4'-(phenylene-1,3-dioxy)dinaphthalene-1,8:1',8'-tetracarboxylic Imide (TfSPODNI)

After adding 1.00 g of HPODNI and 0.53 g of potassium carbonate anhydride in 40 mL of DMF in a 100 mL flask under $N_2$, the mixture was cooled to −5 to −10° C., and then 0.85 g of trifluoromethanesulfonyl chloride was added slowly for 30 min. After stirring, the same for 30 min, the reaction was performed for 2 hr at room temperature. After adding 100 mL of methylene chloride, the same was washed with 2% of sodium bicarbonate solution and distilled water, consecutively. After distilling the solvent under reduced pressure, the product was recrystallized with a mixture of methylene chloride and hexane to obtain 0.67 g (45%) of N,N'-ditifluoroethanesulfonyloxy-4,4'-(phenylene-1,3-dioxy)dinaphthalene-8:1',8'-tetracarboxylic Imide (TfSPODNT).

$^1$H-NMR δ 8.84 (d, 2H), 8.71 (d, 2H), 8.59 (d, 2H), 8.00 (t, 2H), 7.70 (t, 1H), 7.43 (s, 1H), 7.36 (d, 2H), 7.26 (d, 2H).

EXAMPLE 2

Preparation of N,N'-Ditrifluoromethanesulfonyloxy-4,4'-oxydiphthalic Imide (TfSODPI)

(1) Preparation of N,N'-Dihydroxy-4,4'-oxydiphthalic Imide (HODPI)

After adding 3.10 g of 4,4'-oxydiphthalic acid anhydride and 1.53 g of hydroxylamine hydrochloride in 40 mL of pyridine in a 100 mL flask equipped with a condenser and a thermometer under $N_2$, the same was heated to 90° C. and stirred for 2 hr. After distilling pyridine under reduced pressure following the reaction, the same was precipitated in 1N of acetic acid. After filtering, the same, it was washed with distilled water and dried at 100° C. to obtain 3.23 g (95%) of N,N'-dihydroxy-4,4'-oxydiphthalic imide (HODPI).

(2) Preparation of N,N'-Ditrifluoromethanesulfonyloxy-4,4'-oxydiphthalic Imide (TfSODPI)

40 mL of DMF, 1.36 g of HODPI and 1.69 g of trifluoromethanesulfonyl chloride was added in a 100 mL flask under N2. After cooling this mixture to −5~10° C., 1.21 g of triethylamine was added slowly. After stirring the same for 30 min, the reaction was performed for 3 hr at room temperature. After adding 100 mL of methylene chloride in the reaction mixture, the same was washed with 2% of sodium bicarbonate solution and distilled water, consecutively. After distilling the solvent under reduced pressure, the product was recrystallized with a mixture of methylene chloride and hexane to obtain 1.69 g (70%) of N,N'-ditifluoroethanesulfonyloxy-4,4'-oxydiphthalic imide (TfSODPI).

EXAMPLE 3

Preparation of N,N'-Ditrifluoromethanesulfonyloxy-4,4'-isopropylidenediphthalic Imide (TfS-IDI)

(1) Preparation of N,N'-Dihydroxy-4,4'-isopropylidenediphthalic Imide (H-IDI)

After adding 3.36 g of 4,4'-isopropylidenediphthalic acid anhydride and 1.53 g of hydroxylamine hydrochloride in 40 mL of pyridine in a 100 mL flask equipped with a condenser and a thermometer under $N_2$, the same was heated to 90° C. and stirred for 2 hr. After the reaction, pyridine was distilled under reduced pressure, and the product was precipitated in 1N of acetic acid. After filtering and washing with distilled water, the same was dried at 100° C., to obtain 3.40 g (93%) of N,N'-dihydroxy-4,4'-isopropylidenediphthalic imide (H-IDI).

(2) Preparation of N,N'-Ditrifluoromethanesulfonyloxy-4,4'-isopropylidenediphthalic Imide (TfS-IDI)

40 mL of DMF, 1.46 g of H-IDI and 1.69 g of trifluoromethanesulfonyl chloride were added in a 100 mL flask under $N_2$. After cooling this mixture to −5~10° C., 1.21 g of triethylamine was added slowly. After stirring the same for 30 min, the reaction was performed for 3 hr at room temperature. After adding 100 mL of methylene chloride in the reaction mixture, the same was washed with 2% of sodium bicarbonate solution and distilled water, consecutively. After distilling the solvent under reduced pressure, the product was recrystallized with a mixture of methylene chloride and hexane to obtain 1.89 g (75%) of N,N'-ditrifluoromethanesulfonyloxy-4,4'-isopropylidenediphthalic imide (TfS-IDI).

EXAMPLE 4

Preparation of N,N'-Ditrifluoromethanesulfonyloxy-1,4,5,8-naphthalic Diimide (TfSDHNI)

(1) Preparation of N,N'-Dihydroxy-1,4,5,8-naphthalic Diimide (DHNI)

After adding 80 mL of m-cresol and 10.00 g of naphthalene-1,4,5,8-tetracarboxylic dianhydride in a 250 mL flask equipped with a condenser and a thermometer under $N_2$, the same was heated to 90° C. while stirring. After adding 5.56 g of hydroxylamine hydrochloride in the solution, the same was heated to 150° C. and stirred for 12 hr. After precipitating the reaction mixture in 500 mL of methanol and filtering the precipitate, it was recrystallized with DMF and dried at 100° C. to obtain 9.35 g (84%) of N,N'-dihydroxy-1,4,5,8-naphthalic imide (DHNI).

(2) Preparation of N,N'-Ditrifluoromethanesulfonyloxy-1,4,5,8-naphthalic Diimide (TfSDHNI)

After placing 40 mL of DMF, 1.21 g of DHNI and 1.11 g of potassium carbonate anhydride in a 100 mL flask under $N_2$, this mixture was cooled to −5 to −10° C., and 1.69 g of trifluoromethanesulfonyl chloride was added slowly for 30 min. After stirring the same for 30 min, the reaction was performed for 3 hr at room temperature. After adding 100 mL of methylene chloride in the reaction mixture, the same was washed with 2% of sodium bicarbonate solution and distilled water, consecutively. After distilling the solvent under reduced pressure, the product was recrystallized with a mixture of methylene chloride and hexane to obtain 1.58 g (70%) of N,N'-ditrifluoromethanesulfonyloxy-1,4,5,8-naphthalic imide (TfSDINI).

EXPERIMENTAL EXAMPLE 1

After dissolving PAOF-1-4 among polyamide oligomers prepared from Preparing Example 2, N,N'-ditrifluoromethanesulfonyloxy-4,4'-(phenylene-1,3-dioxy)dinaphthalene-1,8:1',8'-tetracarboxylic imide (TfSPODNI) prepared form Example 1 as a photo acid-generating agent, and N,N'-ditrifluoromethanesulfonyloxy-4,4'-oxydiphthalic imide (TfSODPI) prepared from Example 2 in 150 mL of γ-butyrolactone with the content as in the following Table 4, the mixture was filtered through a 0.25 μm membrane filter. After spin-coating this solution in a silicon wafer, it was acceleration-dried at 50° C. for 5 min to obtain a insulation film. Then, UV was exposed for 30 s through photomask using a UV light-exposing device equipped with a 365 nm filter. After heating at 90° C. for 1 min, the mixture was developed in 2.38 wt % of tetramethylammonium hydroxide (TMAH) developer, and was washed with water. This pattern-formed wafer was baked in a 350° C. oven to obtain a hardened pattern. To identify the resolution, the depth and width of the film was measured using a profilo meter and the cross-section was observed with a scanning electronic microscope. The result is shown in Table 4.

TABLE 4

| Photo acid generating agent | | Residual film thickness ratio* (%) | Resolution | | Heat Resistance (TGA) | Remarks |
|---|---|---|---|---|---|---|
| | | | Depth | Width | | |
| TfSPODNI | 0.1 wt % | 87% | — | — | 525° C. | No formation of pattern |
| | 1.0 wt % | 85% | 8 μm | 4 μm | 529° C. | — |

TABLE 4-continued

| Photo acid generating agent | Residual film thickness ratio* (%) | Resolution Depth | Resolution Width | Heat Resistance (TGA) | Remarks |
|---|---|---|---|---|---|
| | 3.0 wt % | 84% | 8 μm | 3 μm | 532° C. | — |
| | 5.0 wt % | 80% | 8 μm | 3 μm | 535° C. | — |
| | 15 wt % | 78% | 7 μm | 5 μm | 530° C. | — |
| | 30 wt % | 65% | — | 10 μm | 523° C. | Partial formation of pattern on the surface |
| TfSODPI | 3.0 wt % | 84% | 7 μm | 4 μm | 532° C. | — |
| | 5.0 wt % | 86% | 8 μm | 5 μm | 534° C. | — |

TfSPODNI:

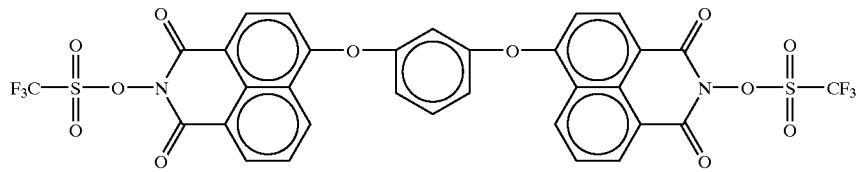

TfSODPI:

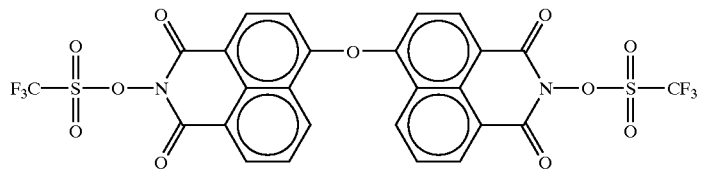

*residual film thickness ratio: the thickness ratio between the film thickness after lithography and curing process and the film thickness after coating.

EXPERIMENTAL EXAMPLE 2

The coating solution was prepared as in Experimental Example 1, however, with different content of tetrahydropyranyl ester added as pendent group polymerized in Preparing Examples 1 and 2. Using 3 wt % of N,N'-ditrifluoromethanesulfonyloxy-4,4'-(phenylene-1,3-dioxy)dinaphthalene-1,8:1',8'-tetracarboxylic imide (TfSPODNI) prepared in Example 1 as photo acid-generating agent, dissolving, coating, drying, developing and hardening was performed with the same method as in Experimental Example 1. Light-exposure time was 10 s, 15 s, 110 s and 200 s, respectively. The result is shown in the following Table 5.

TABLE 5

| Concentration of 3,4-Dihydro-2H-pyran | Exposure time | Developing Time | Residual film thickness ratio | Resolution Depth | Resolution Width | Heat Resistance (TGA) |
|---|---|---|---|---|---|---|
| 1 equiv. | 10 sec | 10 sec | 80% | 8 μm | 3 μm | 528° C. |
| 2 equiv. | 15 sec | 25 sec | 87% | 7 μm | 3 μm | 530° C. |
| 12 equiv. | 110 sec | 15 min | 85% | 8 μm | 5 μm | 534° C. |
| 20 equiv. | 200 sec | 2 hr | 83% | 10 μm | 5 μm | 527° C. |

EXPERIMENTAL EXAMPLE 3

The coating solution was prepared as in Experimental Example 1, however, the polymers prepared in Preparing Examples 1–3 were used. Using 3 wt % N,N'-ditrifluoromethanesulfonyloxy-4,4'-(phenylene-1,3-dioxy)dinaphthalene-1,8:1',8'-tetracarboxylic imide (TfSPODNI) prepared in Example 1 as photo acid-generating agent, dissolving, coating, drying, developing and hardening was performed with the same method as in Experimental Example 1. Light-exposure time was 30 s. The result is shown in the following Table 6.

TABLE 6

| Polymer | Residual film thickness ratio | Resolution Depth | Resolution Width | Heat Resistance |
|---|---|---|---|---|
| PAMF-1-4 | 84% | 9 μm | 3 μm | 529° C. |
| PAmPF-2-4 | 85% | 8 μm | 3 μm | 534° C. |
| PAOM-1-4 | 83% | 9 μm | 3 μm | 536° C. |

EXPERIMENTAL EXAMPLE 4

The coating solution was prepared as in Experimental Example 1, however, the polymers prepared in Preparing Examples 6 and 7 were used. Using 3 wt % of N,N'-ditrifluoromethanesulfonyloxy-4,4'-(phenylene-1,3-dioxy)dinaphthalene-1,8:1',8'-tetracarboxylic imide (TfSPODNI) prepared in Example 1 as photo acid-generating agent, dissolving, coating, drying, developing and hardening was performed with the same method as in Experimental Example 1. Light-exposure time was 30 s. The result is shown in the following Table 7.

TABLE 7

| Alkyl Vinyl Ether | Used Amount of Acid-sensitive Group | Residual film thickness ratio | Resolution Depth | Resolution Width | Heat Resistance (TGA) |
|---|---|---|---|---|---|
| Ethyl Vinyl Ether | 8 mol equiv. | 83% | 9 μm | 3 μm | 529° C. |
| Propyl Vinyl Ether | 8 mol equiv. | 82% | 8 μm | 5 μm | 531° C. |
| Isopropyl Vinyl Ether | 8 mol equiv. | 80% | 8 μm | 4 μm | 532° C. |
| n-Butyl Vinyl Ether | 8 mol equiv. | 77% | 8 μm | 3 μm | 535° C. |
| tert-Butyl Vinyl Ether | 8 mol equiv. | 77% | 10 μm | 3 μm | 524° C. |
| Cyclohexyl Vinyl Ether | 8 mol equiv. | 76% | 10 μm | 4 μm | 536° C. |
| 2,3-Dihydrofuran | 4 mol equiv. | 79% | 9 μm | 5 μm | 539° C. |

EXPERIMENTAL EXAMPLE 5

After dissolving PAOF-1-4 among polyamide oligomers prepared from Preparing Example 2 and N,N'-ditrifluoromethanesulfonyloxy-4,4'-isopropylidenediphthalic imide (TfS-IDI) prepared form Example 3 as a photo acid-generating agent in 150 mL of γ-butyrolactone with the content as in the following Table 8, the mixture was filtered through a 0.25 μm membrane filter. After spin-coating this solution in a silicon wafer, it was acceleration-dried at 50° C. for 5 min to obtain a insulation film. Then, UV was exposed for 30 s through photomask using a UV light-exposing device equipped with a 365 nm filter. After heating at 90° C. for 1 min, the mixture was developed in 2.38 wt % of tetramethylammonium hydroxide (TMAH) developer, and was washed with water. This pattern-formed wafer was baked in a 350° C. oven to obtain a hardened pattern. To identify the resolution, the depth and width of the film was measured using a profilometer and the cross-section was observed with a scanning electronic microscope. The result is shown in Table 8.

EXPERIMENTAL EXAMPLE 6

After dissolving PAOF-1-4 among polyamide polymers prepared from Preparing Example 2 and N,N'-ditrifluoromethanesulfonyloxy-1,4,5,8-naphthalic diimide (TfSDHNI) prepared form Example 4 as a photo acid-generating agent in 150 mL of γ-butyrolactone with the content as in the following Table 9, the mixture was filtered through a 0.25 μm membrane filter. After spin-coating this solution in a silicon wafer, it was acceleration-dried at 50° C. for 5 min to obtain a insulation film. Then, UV was exposed for 30 s through photomask using a UV light-exposing device equipped with a 365 nm filter. After heating at 90° C. for 1 min, the mixture was developed in 2.38 wt % of tetramethylammonium hydroxide (TMAH) developer, and was washed with water. This pattern-formed wafer was baked in a 350° C. oven to obtain a hardened pattern. To identify the resolution, the depth and width of the film was measured using a profilo meter and the cross-section was observed with a scanning electronic microscope. The result is shown in Table 9.

TABLE 8

| Photo acid-generating agent | | Residual film thickness ratio* | Resolution Depth | Resolution Width | Heat Resistance (TGA) |
|---|---|---|---|---|---|
| TfS-IDI | 3 wt % | 85% | 7 μm | 4 μm | 537° C. |
|  | 5 wt % | 88% | 7 μm | 4 μm | 538° C. |

TfS-IDI

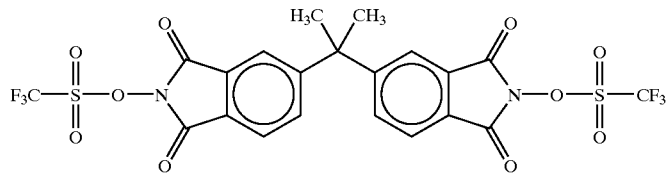

*residual film thickness ratio: the thickness ratio between the film thickness after lithography and curing process and the film thickness after coating.

TABLE 9

| Photo acid-generating agent | | Residual film thickness ratio | Resolution | | Heat Resistance (TGA) | Remarks |
|---|---|---|---|---|---|---|
| | | | Depth | Width | | |
| TfSDHNI | 0.1 wt % | 88% | — | — | 527° C. | No formation of pattern |
| | 1.0 wt % | 84% | 8 μm | 3 μm | 531° C. | — |
| | 3.0 wt % | 82% | 8 μm | 3 μm | 530° C. | — |
| | 5.0 wt % | 82% | 7 μm | 3 μm | 532° C. | — |
| | 15 wt % | 79% | 8 μm | 5 μm | 533° C. | — |
| | 30 wt % | 69% | — | 10 μm | 522° C. | Partial formation of pattern on the surface |

TfSDHNI:

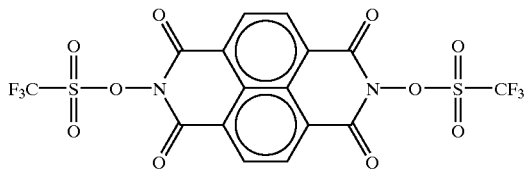

COMPARATIVE EXAMPLE

After dissolving PamPF-2-4, which is a polyamide polymer prepared from Preparing Example 4, and N-trifluoromethanesulfonyloxy-1,8-naphthalimide (TfSNI) or p-nitrobenzyl-9,10-dimethoxyanthracene-2-sulfonate (NBAS) as a photo acid-generating agent in 3.0 wt % of γ-butyrolactone, the mixture was filtered through a 0.25 μm membrane filter. After spin-coating this solution in a silicon wafer, it was acceleration-dried at 50° C. for 5 min to obtain a insulation film. Then, UV was exposed for 30 s through photomask using a UV light-exposing device equipped with a 365 nm filter. After heating at 90° C. for 1 min, the mixture was developed in 2.38 wt % of tetramethylammonium hydroxide (TMAH) developer, and was washed with water. This pattern-formed wafer was baked in a 350° C. oven to obtain a hardened pattern. To identify the resolution, the depth and width of the film was measured using a profilometer and the cross-section was observed with a scanning electronic microscope. The result is shown in Table 10.

TABLE 10

| Photo acid-generating agent | Residual film thickness ratio | Resolution | | Heat Resistance (TGA) | Remarks |
|---|---|---|---|---|---|
| | | Depth | Width | | |
| TfSNI | 87% | — | 4 μm | 523° C. | Incomplete pattern formed, and cracked |
| NBAS | 85% | — | 4 μm | 522° C. | Pattern formed, but cracked |

TfSNI:

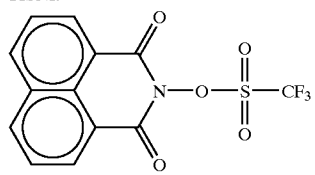

TABLE 10-continued

| Photo acid-generating agent | Residual film thickness ratio | Resolution | | Heat Resistance (TGA) | Remarks |
|---|---|---|---|---|---|
| | | Depth | Width | | |

NBAS:

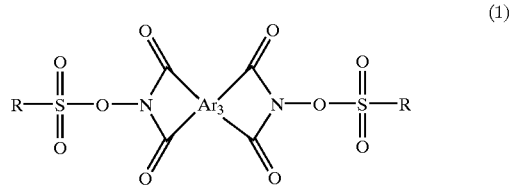

As explained above, the novel photo acid-generating agent according to the present invention and the heat-resistant photoresist composition containing polyamide oligomer having acetal or its cyclized derivative as pendent groups can be used in any application where low-dielectric material is required. Especially, they are useful for passivation layer and buffer coat of semiconductor element or layer-insulating film of the multilayer printed circuit board.

What is claimed is:

1. A photo acid-generating agent expressed by the following formula (1), (1)

$$R-\underset{\underset{O}{\|}}{\overset{\overset{O}{\|}}{S}}-O-N\underset{\underset{O}{\|}}{\overset{\overset{O}{\|}}{\diagdown}}Ar_3\underset{\underset{O}{\|}}{\overset{\overset{O}{\|}}{\diagup}}N-O-\underset{\underset{O}{\|}}{\overset{\overset{O}{\|}}{S}}-R$$

wherein:

represents

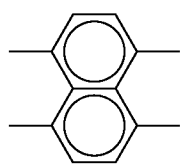 , 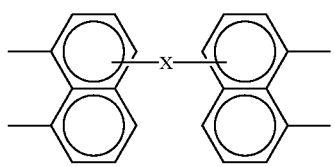 , in which X represents —CH$_2$—, —O—, —S—, —SO$_2$—, —CO—, —NHCO—, —C(CH$_3$)$_2$—, —C(CF$_3$)$_2$—, or

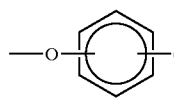 , or 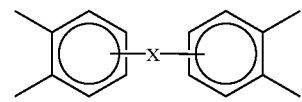 , in which X represents —CH$_2$—, —S—, —SO$_2$—, —CO—, —NHCO—, —C(CH$_3$)$_2$—, or

 ;

and

R represents —CH$_3$, —C$_2$H$_5$, —C$_3$H$_7$, —C$_4$H$_9$, —CF$_3$,

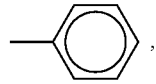 , or 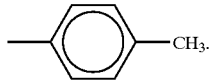 .

2. A photo acid-generating agent according to claim 1, wherein said photo acid-generating agent generates acids by absorbing light with a wavelength longer than the absorption range of polyamide oligomer (i.e., longer than 300 nm).

3. A photo-polymerization method comprising:
   (i) using a photoresist composition comprising an effective amount of a molecular-weight regulator, and (ii) photo-patterning said photoresist composition;
   wherein said molecular weight regulator comprises a photo acid-generating agent expressed by the following formula (1),

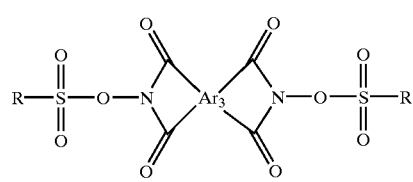

(1)

wherein:

represents

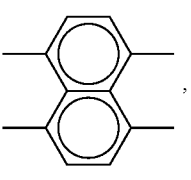 , 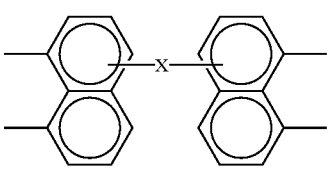 , in which X represents —CH$_2$—, —O—, —S—, —SO$_2$—, —CO—, —NHCO—, —C(CH$_3$)$_2$—, —C(CF$_3$)$_2$—, or

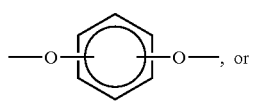 , or 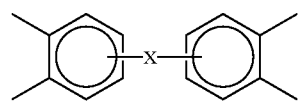 , in which X represents —CH$_2$—, —S—, —SO—, —CO—, —NHCO—, —C(CH$_3$)$_2$—, or

 ;

and

R represents —CH$_3$, —C$_2$H$_5$, —C$_3$H$_7$, —C$_4$H$_9$, —CF$_3$,

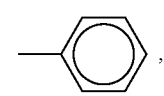 , or 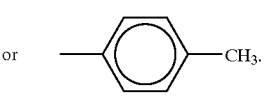 .

4. A heat-resistant photoresist composition comprising:
   (i) an aromatic bis-sulphonic diimide expressed by the following formula (1) as a photo acid-generating agent, and
   (ii) a polyamide oligomer having ester groups as pendent groups expressed by the following formula (2),

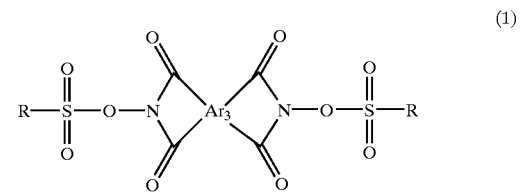

(1)

wherein the composition comprises the aromatic bis-sulphonic diimide expressed by formula (1) in an amount ranging from 0.3 to 15 wt % relative to a weight of the polyamide oligomer having ester groups as pendent groups expressed by formula (2);

represents 
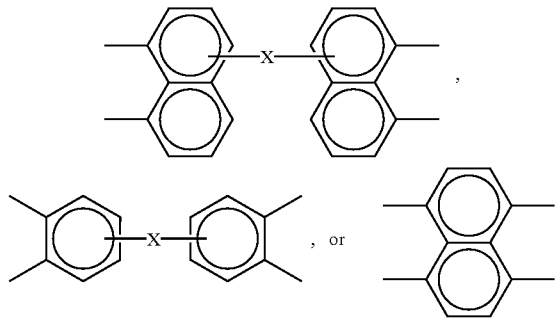
in which X represents —CH$_2$—, —O—, —S—, —SO$_2$—, —CO—, —NHCO—, —C(CH$_3$)$_2$—, —C(CF$_3$)$_2$—, or
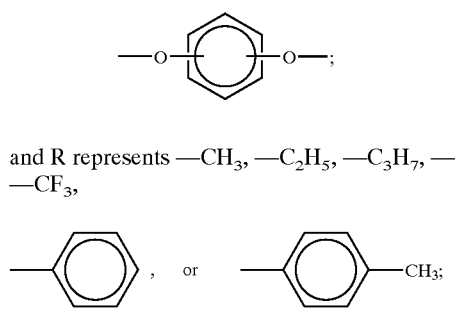
and R represents —CH$_3$, —C$_2$H$_5$, —C$_3$H$_7$, —C$_4$H$_9$, —CF$_3$,
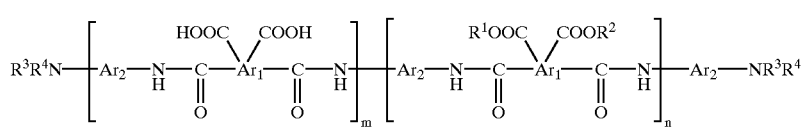
Ar$_2$ is a secondary aromatic group which is selected from the group consisting of
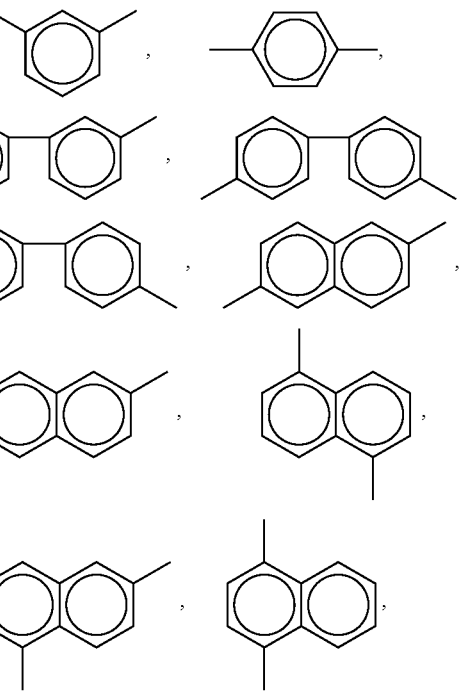
$$\text{(2)}$$
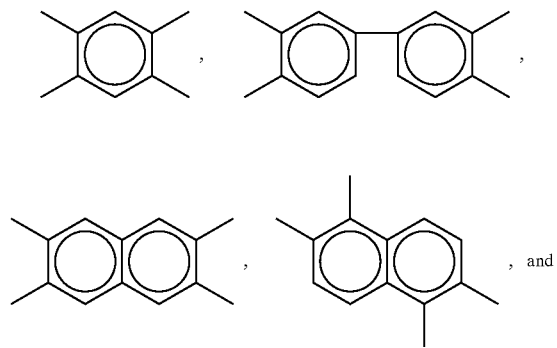
wherein Ar$_1$ is a quaternary aromatic group which is selected from the group consisting of
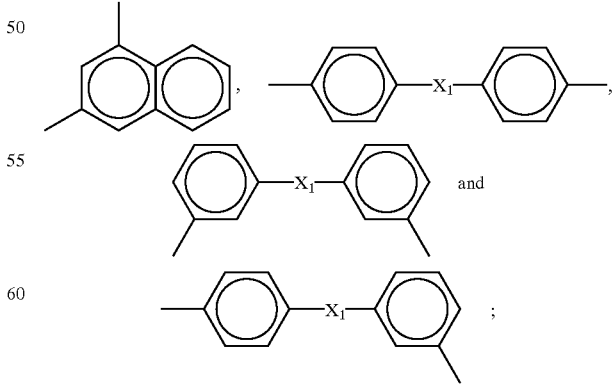
X$_1$ is —CH$_2$—, —O—, —S—, —SO$_2$—, —CO—, —NHCO—, —C(CH$_3$)$_2$—, —C(CF$_3$)$_2$—,

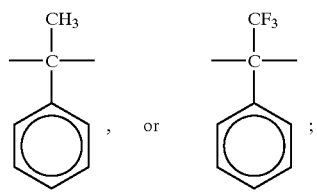, or 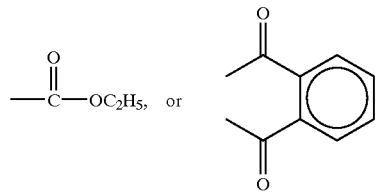;

$R^1$ and $R^2$ are independently a hydrogen atom or $C_1$–$C_{10}$ alkyl having

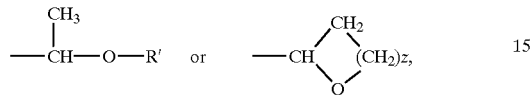

wherein R' is a $C_1$–$C_6$ alkyl such as ethyl, propyl, isopropyl, butyl, isobutyl, t-butyl and cyclohexyl; and z is an integer of 1–4, with the proviso that both $R^1$ and $R^2$ are not hydrogen atoms;

$R^3$ and $R^4$ are independently a hydrogen atom, which exist at the terminal portion of the molecule added to adjust the molecular weight of the oligomer; and a degree of polymerization (m+n) is 3–50.

* * * * *

UNITED STATES PATENT AND TRADEMARK OFFICE
CERTIFICATE OF CORRECTION

PATENT NO. : 6,582,879 B2
DATED : June 24, 2003
INVENTOR(S) : Kil-Yeong Choi et al.

It is certified that error appears in the above-identified patent and that said Letters Patent is hereby corrected as shown below:

<u>Column 22,</u>
Line 27, "SO" should read -- $SO_2$ --.

Signed and Sealed this

Third Day of February, 2004

JON W. DUDAS
*Acting Director of the United States Patent and Trademark Office*